United States Patent [19]

Wagner et al.

[11] Patent Number: 5,569,765
[45] Date of Patent: Oct. 29, 1996

[54] 2-ANILINOPYRIDINE PESTICIDES

[75] Inventors: Oliver Wagner, Bexbach; Karl Eicken, Wachenheim; Eberhard Ammermann, Heppenheim; Gisela Lorenz, Neustadt, all of Germany

[73] Assignee: BASF Aktiengesellschaft, Ludwigshafen, Germany

[21] Appl. No.: 422,862

[22] Filed: Apr. 17, 1995

Related U.S. Application Data

[62] Division of Ser. No. 208,816, Mar. 11, 1994, Pat. No. 5,453,432.

[30] Foreign Application Priority Data

Mar. 17, 1993 [DE] Germany .......................... 43 08 395.1

[51] Int. Cl.$^6$ .................................................. C07D 213/74
[52] U.S. Cl. ........................ 546/304; 546/287; 546/289; 546/297; 546/309; 546/310; 546/312
[58] Field of Search .................................. 546/287, 289, 546/297, 309, 304, 310, 312

[56] References Cited

U.S. PATENT DOCUMENTS

| | | | |
|---|---|---|---|
| 4,331,670 | 5/1982 | Nishiyama et al. | 424/263 |
| 5,154,751 | 10/1992 | Rempfler | 71/94 |

FOREIGN PATENT DOCUMENTS

| | | |
|---|---|---|
| 384311 | 8/1990 | European Pat. Off. . |
| 3731626 | 3/1989 | Germany . |

OTHER PUBLICATIONS

Fusco et al., Chemical Abstracts, vol. 69, 96598z 1968.
Abramovitch et al., J. C. S. Chem. Comm., pp. 956–957 1979.

*Primary Examiner*—Richard L. Raymond
*Attorney, Agent, or Firm*—Keil & Weinkauf

[57] ABSTRACT

A process for controlling pests in which the pests or the plants threatened by attack with pests are treated with a 2-anilinopyridine of the formula I

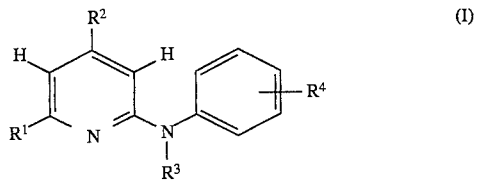

where the substituents have the following meanings:

$R^1$ is alkyl, alkenyl, alkynyl, haloalkyl, alkoxyalkyl, alkylthioalkyl, cycloalkyl, substituted cycloalkyl, alkoxy, haloalkoxy, substituted alkyl, alkenyloxy, alkynyloxy, halogen, CN, SCN, formyl, $CH=NOR_5$, $CH=NR_6$, $CH_2NHR_6$ $R^5$ is hydrogen, unsubstituted or substituted alkyl, alkenyl, alkynyl, $COR^7$ or unsubstituted or substituted phenyl, $R^6$ is hydrogen, alkyl, unsubstituted or substituted cycloalkyl, alkenyl, alkynyl or unsubstituted or substituted phenyl, $R^2$ is alkyl, alkenyl, alkynyl, haloalkyl or cycloalkyl $R^3$ is hydrogen, CN, $S(O)_nR^8$ or $COR^9$, $R^8$ is alkyl or substituted phenyl, $R^9$ is hydrogen, alkyl, haloalkyl, cycloalkyl, phenyl or benzyl, $R^4$ is hydrogen, halogen, alkyl, haloalkyl, alkoxy or haloalkoxy or cyano, and 2-anilinopyridines and also use of the compounds for the production of pesticides are described.

3 Claims, No Drawings

2-ANILINOPYRIDINE PESTICIDES

This is a divisional of application Ser. No. 08/208,816, filed Mar. 11, 1994, now U.S. Pat. No. 5,453,432.

The present invention relates to the use of anilinopyridines of the general formula I

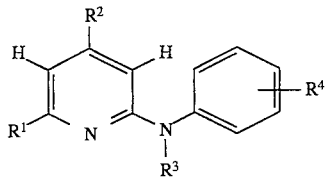

where the substituents have the following meanings:

$R_1$ is $C_1$–$C_6$-alkyl, $C_2$–$C_4$-alkenyl, $C_2$–$C_4$-alkynyl, $C_1$–$C_6$-haloalkyl, $C_1$–$C_6$-alkoxy-$C_1$–$C_6$-alkyl, $C_1$–$C_6$-alkylthio-$C_1$–$C_6$-alkyl or $C_3$–$C_6$-cycloalkyl;

$C_3$–$C_6$-cycloalkyl, $C_1$–$C_6$-alkoxy or $C_1$–$C_6$-haloalkoxy substituted up to three times by identical or different $C_1$–$C_2$-alkyl or halogen substituents;

$C_1$–$C_2$-alkyl, $C_2$–$C_4$-alkenyloxy or $C_2$–$C_4$-alkynyloxy substituted by hydroxyl;

halogen, CN, SCN, formyl, CH=NOR$^5$, CH=NR$^6$, $CH_2NHR^6$ $R_5$ is hydrogen, $C_1$–$C_8$-alkyl;

$C_1$–$C_4$-alkyl which is substituted by halogen, hydroxyl, cyano, $C_1$–$C_4$-alkoxy, $COOC_1$–$C_3$-alkyl or by phenyl, it being possible for the phenyl to be substituted by halogen, $C_1$–$C_3$-alkyl, $C_1$–$C_3$-alkoxy or nitro;

$C_3$–$C_6$-alkenyl, $C_3$–$C_6$-alkenyl substituted by halogen, $C_3$–$C_6$-alkynyl, $C_3$–$C_6$-alkynyl substituted by halogen, phenyl or phenyl substituted one to three times by halogen, $C_1$–$C_3$-alkyl, $C_1$–$C_3$-alkoxy or nitro or an acyl radical $COR^7$ where $R^7$ is $C_1$–$C_6$-alkyl or $C_1$–$C_6$-alkyl substituted by halogen or $C_1$–$C_3$-alkoxy, $C_3$–$C_6$-alkenyl or $C_3$–$C_6$-alkenyl substituted by halogen;

$R^6$ is hydrogen, $C_1$–$C_6$-alkyl, $C_1$–$C_4$-alkyl which is substituted by halogen, hydroxyl, cyano, $C_1$–$C_4$-alkoxy, $C_1$–$C_4$-alkylamino, $C_3$–$C_6$-cycloalkyl or by phenyl, it being possible for the phenyl to be substituted by halogen, $C_1$–$C_3$-alkyl, $C_1$–$C_3$-alkoxy or nitro;

$C_3$–$C_6$-cycloalkyl or $C_3$–$C_6$-cycloalkyl substituted by methyl;

$C_3$–$C_6$-alkenyl or $C_3$–$C_6$-alkenyl substituted by halogen; $C_3$–$C_6$-alkynyl or $C_3$–$C_6$-alkynyl substituted by halogen;

phenyl or phenyl substituted by halogen, $C_1$–$C_3$-alkyl, $C_1$–$C_3$-alkoxy, $C_1$–$C_2$-haloalkyl, $C_1$–$C_2$-haloalkoxy or nitro;

$R^2$ is $C_1$–$C_6$-alkyl, $C_2$–$C_4$-alkenyl, $C_2$–$C_4$-alkynyl, $C_1$–$C_6$-haloalkyl, $C_3$–$C_6$-cycloalkyl or $C_3$–$C_6$-cycloalkyl substituted up to three times by identical or different $C_1$–$C_2$-alkyl or halogen substituents, $R^3$ is hydrogen, CN, $S(O)_nR^8$ where n=0, 1 or 2, or $COR^9$ $R^8$ is $C_1$–$C_3$-alkyl, or phenyl; optionally substituted 1 to 3 times by halogen, $C_1$–$C_2$-alkyl, $C_1$–$C_2$-haloalkyl, methoxy or nitro, $R^9$ is hydrogen, $C_1$–$C_6$-alkyl, $C_1$–$C_6$-haloalkyl, $C_3$–$C_6$-cycloalkyl, phenyl or benzyl, or phenyl substituted 1 to 3 times by halogen, $C_1$–$C_3$-alkyl, $C_1$–$C_3$-haloalkyl, $C_1$–$C_3$-alkoxy, nitro or cyano, or benzyl substituted by these radicals, $R^4$ is hydrogen, halogen, $C_1$–$C_3$-alkyl, $C_1$–$C_2$-haloalkyl, $C_1$–$C_3$-alkoxy or $C_1$–$C_3$-haloalkoxy or cyano, for controlling pests.

The individual radicals are, for example:

halogen is: fluorine, chlorine, bromine or iodine.

Alkyl itself or as a constituent of another subtituent, such as haloalkyl, alkoxy or haloalkoxy, is to be understood, depending on the number of carbon atoms named, as meaning, for example: methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, particularly preferably methyl, it being possible for the alkyl to carry one to three halogen atoms, such as eg. $CHCl_2CH_2F$, $CCl_3$, $CH_2Cl$, $CHF_2$, $CH_2CH_2Br$, $C_2Cl_5$, $CH_2Br$, CHBrCl, preferably $CF_3$.

Cycloalkyl is cyclopropyl, cyclobutyl, cyclopentyl or cyclohexyl, particularly preferably cyclopropyl, it being possible for the cycloalkyl to be unsubstituted or substituted by 1–3 $C_1$–$C_2$-alkyl radicals or halogen.

Alkenyl is eg. 1-propenyl, allyl, 1-butenyl, 2-butenyl, 3-butenyl, 1-methyl-2-propenyl or 2-methyl-2-propenyl, alkynyl is eg. 1-propynyl, 2-propynyl, 1-butynyl or 2-butynyl, preferably 1-propynyl.

The following are to be mentioned as particularly preferred individual compounds for application:

2-anilino-4,6-dimethylpyridine,
2-(3-fluoroanilino)-4,6-dimethylpyridine,
2-anilino-6-cyclopropyl-4-methylpyridine,
2-(3-fluoroanilino)-6-cyclopropyl-4-methylpyridine.

The invention further relates to novel 2-anilinopyridines of the general formula I as claimed in claim 1 with the exception of the following compounds where the radicals $R^1$, $R^2$, $R^3$ and $R^4$ have the following meanings:

| $R^1$ | $R^2$ | $R^3$ | $R^4$ |
|---|---|---|---|
| $CH_3$ | $CH_3$ | H | 2-F |
| $CH_3$ | $CF_3$ | H | 2-F |
| $CH_3$ | $CH_3$ | H | 3-F |
| $CH_3$ | $CF_3$ | H | 3-F |
| $CF_3$ | $CH_3$ | H | 3-F |
| Cl | $CF_3$ | H | H |
| $CH_3$ | $CH_3$ | H | H |
| $CH_3$ | $CH_3$ | CN | H |
| $CH_3$ | $CH_3$ | Phenyl-CO | H |
| $CH_3$ | $CF_3$ | H | H |

It is known that 2-anilino-3-cyanopyridines (DE-A 3 731 626) have fungicidal action. Their action, however, is unsatisfactory. N-Phenyl-N-pyridin-2-ylureas having herbicidal and plant growth-regulating action are also known (EP-A 401 168). However, no fungicidal action is described for them.

It has now surprisingly been found that 2-anilinopyridines of the formula I as in claim 1 have a potent action against pests, in particular fungi, in particular phytopathogenic fungi, in particular *Botrytis cinerea*.

The compounds of the general formula I are prepared, for example, as described in the following schemes:

The compounds of the formula I are obtained, for example, by reacting the pyridine-N-oxides 1a with the respective aniline derivatives 1b in the presence of alkyl- or arylsulfonyl chlorides, preferably tosyl chloride, in the presence of a basic catalyst such as eg. alkali metal hydroxides, preferably sodium hydroxide or potassium hydroxide. The acid-catalyzed hydrolysis of the N-tosylanilinopyridines 1c yields the anilinopyridines I (cf. eg.: Yu. V. Kurbatov, M.A. Solekhova, Khim. Getero. Soedin., 7 (1986) 936).

The precursors 1a are known in some cases. They are prepared by processes described in the literature (see eg. R.

A. Abramovitch, Heterocyclic Compounds, Pyridine and its Derivatives Vol 14, Part 1–4, Ed: A. Weissberger, E. C. Taylor and literature cited there).

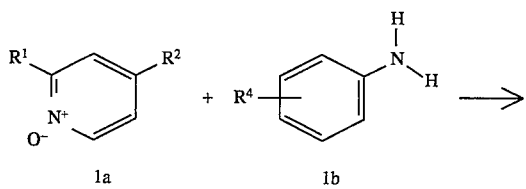

1a      1b

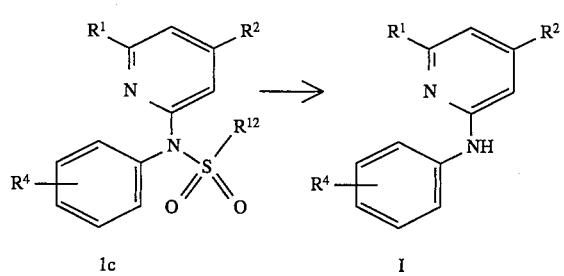

1c      I

Alternatively to this, compounds of the formula I can be obtained by reacting halobenzenes 1d with 2-anilinopyridines 1e under the action of base. Suitable bases are, for example, alkali metal hydrides, eg. sodium hydride or potassium hydride, or alkali metal amides, eg. sodium amide or potassium amide.

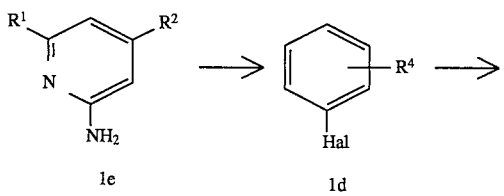

1e      1d

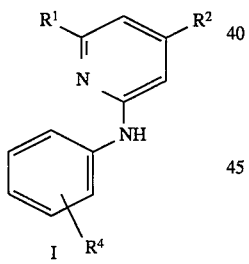

I

In addition, compounds of the general formula I can be prepared by reacting anilines 1f with the pyridine derivatives 1g with or without addition of base (cf. eg. D. M. Bailey et al., J. Med. Chem., 14 (1971) 439).

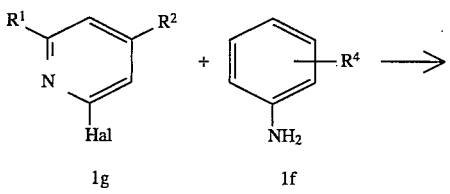

1g      1f

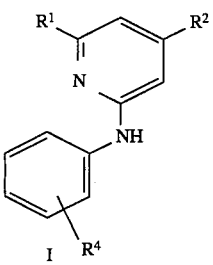

A further variant consists in reacting the pyridines 1h with α-halo-α-phenylhydrazonoacetic acid esters 1i, preferably α-chloro-α-phenylhydrazonoacetic acid t-butyl ester. The hydrolysis of the resulting N-cyanoanilinopyridines 1j with addition of base yields the anilinopyridines I (R. Fusco et al. Gazz. chim. ital., 98 (1968) 511).

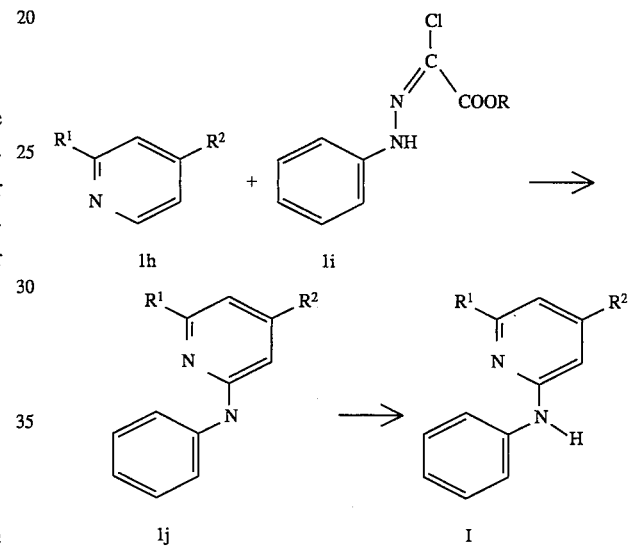

1h      1i

1j      I

Compounds of the general formula 3 can be prepared, for example, by converting compounds of the general formula 1 where $R^1=CH_3$ by known processes using oxidants such as eg. hydrogen peroxide or peracids, preferably m-chloroperbenzoic acid, in protic solvents, preferably acetic acid, or in aprotic solvents, eg. dichloromethane, into the N-oxides 2 which, by reaction with alkylcarboxylic anhydrides, eg. acetic anhydride, and subsequent basic hydrolysis of the acyl intermediate, afford the hydroxymethylene compound 3 (see eg. D. Bailey et al., J. Med. Chem., 14 (1971) 439).

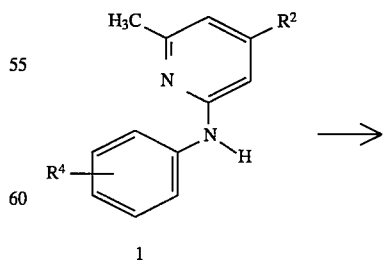

1

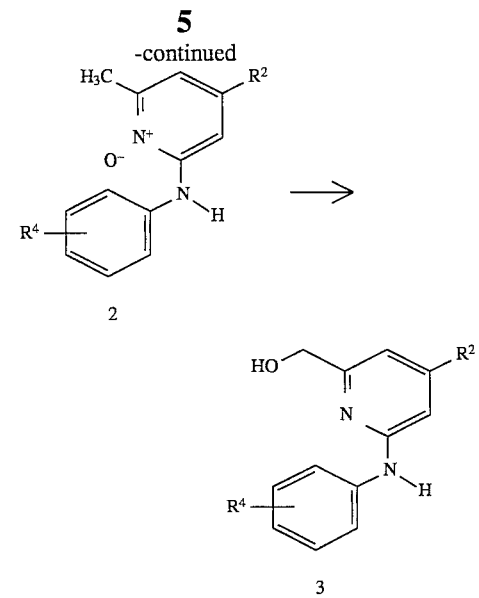

Compounds of the general structure 4, where Hal is fluorine, chlorine, bromine or iodine, are accessible from the corresponding hydroxide compounds 3 by processes known from the literature (eg. Houben-Weyl, Methoden der Organischen Chemie (Methods of Organic Chemistry), 4th edition, volume 5/3 and 4, Halogen Compounds).

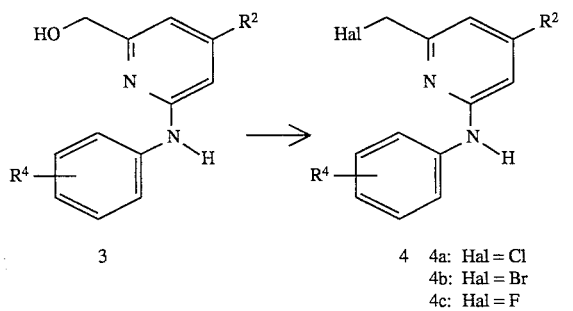

A possible preferred process in this case for preparing the halides (Cl, Br) 4a,b is the reaction of the hydroxymethylene compound 4 with suitable halogenating agents, eg. thionyl chloride or thionyl bromide or with halogen compounds of tri- or penta-valent phosphorus (eg. $PBr_3$, $PCl_3$) in the presence or absence of a proton acceptor in the presence of an inert solvent, eg. hydrocarbons such as petroleum ether, cyclohexane, benzene, toluene or xylene. The reaction is carried out at from −20° C. to the boiling point of the corresponding solvent, with or without catalyst. Suitable catalysts are, for example, DMF or tertiary amines such as triethylamine, N,N-dimethylaniline or piperidine.

For preparation of the fluorides 4c, the hydroxymethylene compounds 3 are reacted at room temperature with a fluorinating agent, eg. diethylaminosulfur trifluoride, in an inert solvent, eg. dichloromethane.

Compounds of the general structure 5, where alkyl-X is $C_1$-$C_6$-alkoxy (eg. —$CH_2$—O—alkyl where alkyl is eg. methyl, ethyl or isopropyl) or $C_1$-$C_6$-alkylthio (eg. $CH_2$—S—alkyl where alkyl is eg. methyl, ethyl or isopropyl), can be obtained by reacting the compounds 4 with an alcohol (eg. methanol, ethanol or isopropanol), preferably in an inert solvent or in an excess of the alcohol concerned which simultaneously serves as a diluent, in the presence of a base (eg. alkali metals, their hydroxides or hydrides) in a temperature range which is from −20° C. to the boiling point of the appropriate solvent.

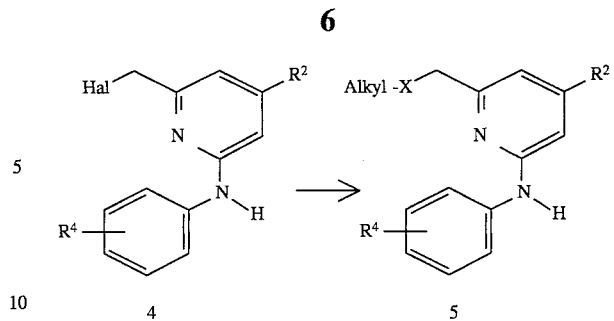

Compounds of the general formula 6 can be prepared starting from the hydroxymethylene compounds 3 by generally known processes (see eg. Houben-Weyl, Methoden der Organischen Chemie (Methods of Organic Chemistry), 4th edition, E3, 265 ff).

The preferred process used is oxidation with dimethyl sulfoxide in the presence of suitable auxiliary reagents, eg. oxalyl chloride/triethylamine. Possible diluents are inert organic solvents, eg. hydrocarbons such as petroleum ether, cyclohexane, benzene or chlorinated hydrocarbons such as dichloromethane, chloroform or 1,2-dichloroethane, or ethers such as eg. diethyl ether, tetrahydrofuran or dioxane. The reaction is carried out in a range from −80° C. to 50° C., preferably −70° C. to −10° C.

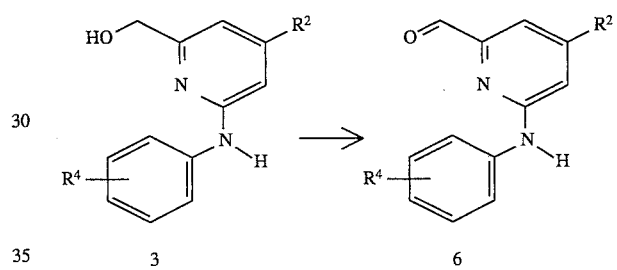

The oxime ethers of the general formula 7 are accessible by processes known per se (see Houben-Weyl, Methoden der Organischen Chemie (Methods of Organic Chemistry), 4th edition, volume 10/4 p. 55 ff). The preferred process used is the reaction of the aldehydes of the general formula 6 with a hydroxylamine $H_2N$—O—$R^5$ or the corresponding hydrochloride (eg. H, methyl, ethyl, hydroxyethyl, haloethyl, benzyl or benzyl substituted by fluorine, chlorine or methyl, $C_3$–$C_4$-alkenyl, $C_3$–$C_4$-alkynyl or $CH_2Ph$) in a suitable diluent and suitable auxiliary reagents.

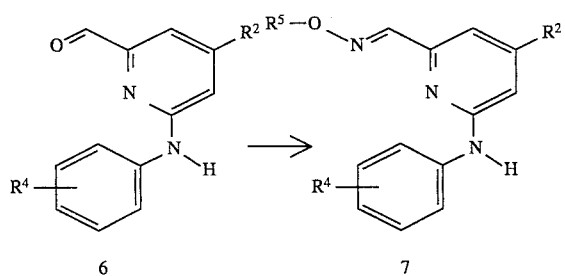

Possible diluents are solvents such as chlorinated hydrocarbons, eg. dichloromethane, 1,2-dichloroethane or alcohols, such as eg. methanol, ethanol, isopropanol or nitriles such as acetonitrile, propionitrile and water. Possible reaction auxiliaries are inorganic and organic bases, eg. alkali metal hydroxides, such as eg. sodium hydroxide, or alkali metal alkoxides, such as eg. sodium methoxide or alkali metal carbonates such as eg. sodium carbonate and potassium carbonate, or tertiary amines: triethylamine. The reaction is carried out at from 0° C. to the boiling point of the diluent employed, preferably 20° C.–80° C.

Compounds of the general formula 8 ($R^6$ eg. $C_1$–$C_6$-alkyl, preferably methyl, ethyl, propyl or $C_3$–$C_6$-cycloalkyl, eg. cyclopropyl, cyclopentyl, cyclohexyl or $C_1$–$C_2$-alkyl substituted by chlorine, hydroxyl, cyclopropyl or benzyl, or allyl, propargyl and also phenyl or phenyl substituted by fluorine, chlorine, methyl or trifluoromethyl) can be prepared by reacting a compound of the general formula 6 with a primary amine of the formula $H_2N$—$R^6$ in which $R^6$ has the meanings described above, in an inert solvent, eg. hydrocarbons: petroleum ether or cyclohexane, preferably toluene, benzene or xylene, in the presence of a reaction auxiliary (eg. small amounts of inorganic or organic acids, eg. toluenesulfonic acid), at from 0° C. to the boiling point of the respective diluent preferably from 80° to 120° C.

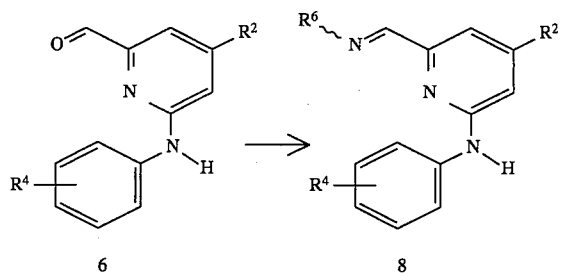

Compounds of the general formula 9 can be prepared by hydrogenation of the compounds 8 with elemental hydrogen under normal pressure or with overpressure in the presence of a catalyst, eg. palladium-carbon or Raney nickel in an inert solvent, eg. ethyl acetate, tetrahydrofuran or dioxane at 10° C.–120° C, preferably 20° C.–60° C. (see eg. Houben-Weyl, Methoden der Organischen Chemie (Methods of Organic Chemistry), volume 11/1 p. 602 ff).

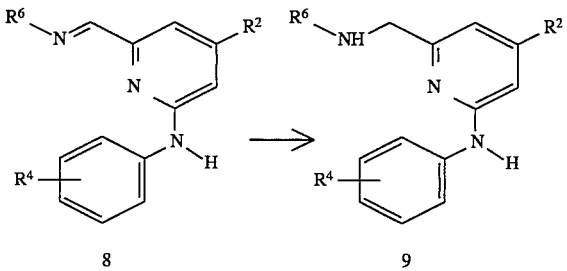

Compounds of the general formula 10 where $R^1$=CN can be prepared from compounds of the general formula 7 where $R^5$=H (7a) by processes known per se (see eg. Houben-Weyl, Methoden der organischen Chemie (Methods of Organic Chemistry), 4th edition, volume E5, p. 1346), the aldoximes being reacted in the presence of a solvent (eg. acetonitrile or dichloromethane) with a dehydrating agent (eg. acetic anhydride, trichloromethyl chloroformate, trichloroacetyl chloride, $SOCl_2$, etc.) at –20° C.–50° C., preferably 0° C.–20° C.

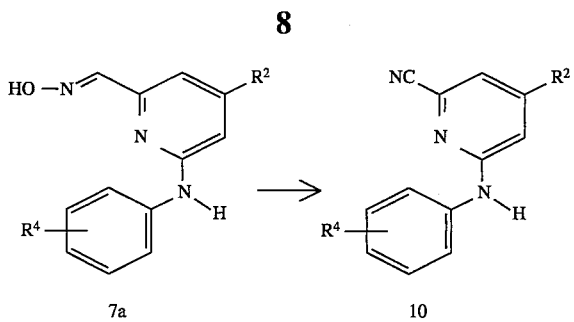

Compounds of the general formula 1j can, on the one hand, be obtained as described above starting from 2,4-disubstituted pyridines 1h, by reaction with α-chloro-α-phenylhydrazonoacetates. Alternatively to this, the compounds can be obtained starting from compounds of the general formula 1 in which the substituents have the meanings described in claim 1 and $R^3$ is hydrogen, by reaction with cyanogen bromide in an inert solvent, eg. diethyl ether, tetrahydrofuran, dimethylformamide or dimethyl sulfoxide, in the presence of an organic or inorganic base (see eg. S. Salman et al., Indian J. Chem., 27B (1988) 583).

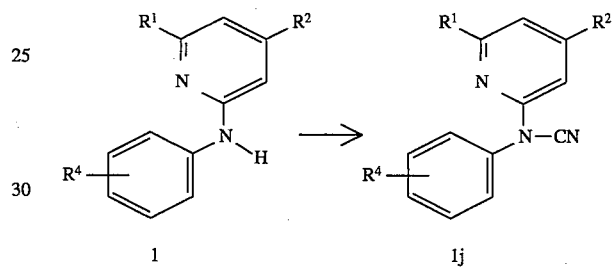

Compounds of the general formula 12 ($R^9$ eg. H, $C_1$–$C_6$-alkyl, (eg. methyl, ethyl or isopropyl) or $C_1$–$C_6$-haloalkyl (eg. trifluorometh or trichlorometh) can be prepared by processes known per se by reacting compounds of the general formula I in which $R^3$ is H with a carboxylic acid derivative. For the preparation of compounds according to the invention, suitable carboxylic acid derivatives are eg. acid chlorides, acid anhydrides or orthocarboxylic acid esters. The acylation of the compounds of the general formula 1 where $R^3$=H can be carried out with or without solvents, it also being possible for the solvent (eg. pyridine) to be used simultaneously as acid acceptor. The acid acceptor used can also be the starting material itself, other organic bases (eg. triethylamine) or inorganic bases.

Solvents suitable for the acylation reaction are all customary solvents (eg. pyridine, dichloromethane, dioxane or tetrahydrofuran).

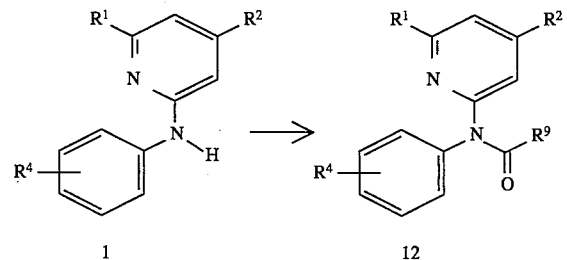

Compounds of the general formula 14, Hal being eg. chlorine or bromine, can be obtained by reacting the N-oxides 13 with phosphorus oxyhalides (halogen is eg. Cl or Br) in an inert solvent or preferably without solvent at from 20° C. to the boiling point of the respective solvent, preferably 70°–120°. (See eg. R. A. Abramovitch, E. M. Smith; Pyridine-1-oxides, in Heterocyclic Compounds, Pyridine and its Derivatives Vol 14, Part 2, pp. 1–261, Ed: A. Weissberger, E. C. Taylor).

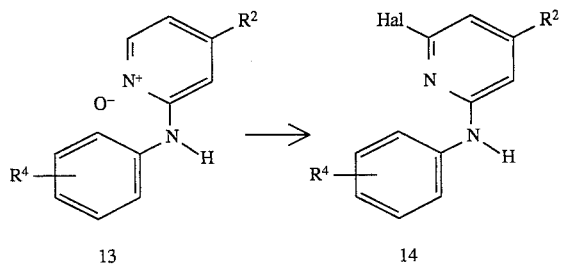

Compounds of the general structure 15, where alkyl-X is $C_1$–$C_6$-alkoxy (eg. O-alkyl where alkyl is eg. methyl, ethyl or isopropyl) or $C_1$–$C_6$-alkylthio (eg. S-alkyl where alkyl is eg. methyl, ethyl or isopropyl), can be obtained by reacting the compounds 14 with an alcohol or a thiol of the general formula HX-alkyl where X=O or S and alkyl has the meanings described above, (eg. methanol, ethanol or isopropanol) preferably in an inert solvent or in an excess of the alcohol concerned, which is used simultaneously as a diluent, in the presence of a base (eg. alkali metals, their hydroxides or hydrides) in a range from −20° C. to the boiling point of the corresponding solvent.

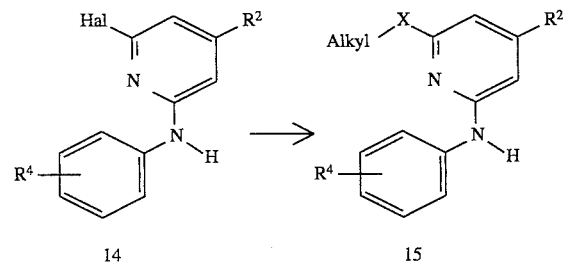

The following examples illustrate the preparation of the novel compounds.

EXAMPLE 1

2-(N-Tosylsulfonyl)anilino-6-cyclopropyl-4-methylpyridine (compound No. 28)

a) 7.74 g (0.045 mol) of m-chloroperbenzoic acid in 125 ml of dichloromethane are added dropwise at room temperature (20° C.) to 5.7 g (0.041 mol) of 2-cyclopropyl-4-methylpyridine in 50 ml of dichloromethane. The mixture is left for 6 h at RT (room temperature), and 3 g of sodium sulfite are then added. After 1 h, the reaction mixture is washed first with saturated sodium carbonate solution and then with water. The wash solution is extracted with dichloromethane, and the organic phases are combined, dried and concentrated. 5.7 g (98%) of 2-cyclopropyl-4-methylpyridine-N-oxide remain as a slightly yellow oil.

b) 22 ml of a 10% NaOH solution (0.054 mol) are added dropwise at RT to 2 g (0.0134 mol) of the oil obtained above, 1.25 g (0.0134 mol) of aniline and 6.48 g (0.034 mol) of toluene-4-sulfonyl chloride in 50 ml of dichloromethane. The mixture is stirred at RT for 24 h, the phases are separated, and the aqueous phase is extracted with dichloromethane. The combined organic phases are dried over sodium sulfate and concentrated. The residual oil is purified by column chromatography (cyclohexane:ethyl acetate=2:1). 3.54 g (70%) of the title compound are obtained as a slightly yellow oil.

EXAMPLE 2

2-Anilino-6-cyclopropane-4-methylpyridine (compound No. 24)

3.2 g (0.0085 mol) of 2-(N-p-toluenesulfonyl)anilino-6-cyclopropyl-4-methylpyridine are taken up in 150 ml of conc. HCl and heated under reflux for 8 h. The solution is then largely concentrated, added to water, neutralized with potassium carbonate and extracted with dichloromethane.

After removing the solvent by distillation, 1.64 g (91.8%) of the title compound remain.

EXAMPLE 3

2-(N-Acetyl)anilino-4,6-dimethylpyridine (compound No. 7)

0.51 g (0.005 mol) of acetic anhydride is added dropwise at RT to 1 g (0.005 mol) of 2-anilino-4,6-dimethylpyridine in 10 ml of glacial acetic acid. The mixture is additionally stirred for 1 h, poured onto water, rendered neutral with 10% NaOH and extracted with dichloromethane. The organic extracts are dried and concentrated. A light brown oil remains, which crystallizes at once (0.64 g; 53%).

The following compounds are suitable, for example, for use according to the claimed process for controlling pests.

TABLE 1

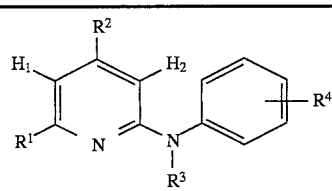

(I)

Me = methyl
Ph = phenyl

| No. | $R^1$ | $R^2$ | $R^4$ | $R^3$ | $^1$H-NMR data ($H_1$ v. $H_2$) |
|---|---|---|---|---|---|
| 1 | Me | Me | 2-F | H | 6.43; 6.47 |
| 2 | Me | Me | 3-F | H | 6.49; 6.59 |
| 3 | Me | Me | 4-F | H | 6.39; 6.44 |
| 4 | Me | Me | 2-F | $SO_2$4-Me—Ph | 6.54; 6.77 |

TABLE 1-continued (I)

Structure: pyridine with R¹ at position 6, R² at position 4, H₁ at position 5, H₂ at position 3, N at position 1; the position 2 nitrogen bears R³ and a phenyl group substituted with R⁴.

Me = methyl
Ph = phenyl

| No. | R¹ | R² | R⁴ | R³ | ¹H-NMR data (H₁ v. H₂) |
|---|---|---|---|---|---|
| 5 | Me | Me | 3-F | SO₂4-Me—Ph | |
| 6 | Me | Me | 4-F | SO₂4-Me—Ph | 6.31; 6.65 |
| 7 | Me | Me | H | CO—CH₃ | 6.87(2H) |
| 8 | Me | Me | H | CO—CH₂C | |
| 9 | Me | Me | H | CO—CHCl₂ | |
| 10 | Me | Me | H | CO—CCl₃ | |
| 11 | Me | Me | H | CO—CH₂Ph | |
|  | Me | Me | H | CO—Et | |
| 12 | CF₃ | Me | H | CN | |
| 13 | CF₃ | Me | 2-F | H | |
| 14 | CF₃ | Me | 3-F | H | |
| 15 | CF₃ | Me | 4-F | H | |
| 16 | CF₃ | Me | H | H | |
| 17 | CF₃ | Me | H | CO—CH₃ | |
| 18 | C₂H₅ | Me | H | H | |
| 19 | C₂H₅ | Me | 2-F | H | |
| 20 | C₂H₅ | Me | 3-F | H | |
| 21 | C₂H₅ | Me | 4-F | H | |
| 22 | C₂H₅ | Me | H | CN | |
| 23 | C₂H₅ | Me | H | CO—Me | |
| 24 | Cyclopropyl | Me | H | H | 6.45(2H) |
| 25 | Cyclopropyl | Me | 2-F | H | |
| 26 | Cyclopropyl | Me | 3-F | H | 6.52; 6.40 |
| 27 | Cyclopropyl | Me | 4-F | H | |
| 28 | Cyclopropyl | Me | H | SO₂4-Me—Ph | 6.55; 6.80 |
| 29 | Cyclroyl | Me | 2-F | SO₂4-Me—Ph | |
| 30 | Cyclopropyl | Me | 3-F | SO₂4-Me—Ph | |
| 31 | Cyclopropyl | Me | 4-F | SO₂4-Me—Ph | 6.67; 6.85 |
| 32 | Cyclopropyl | Me | H | CO—CH₃ | 6.84; 6.90 |
| 33 | Cyclopropyl | Me | H | CN | |
| 34 | Cyclopentyl | Me | H | H | |
| 35 | Cyclopentyl | Me | 3-F | H | 6.45; 6.55 |
| 36 | Cyclobutyl | Me | H | H | |
| 37 | C₃H₇-i | Me | H | H | |
| 38 | C₃H₇-i | Me | 2-F | H | |
| 39 | C₃H₇-i | Me | 3-F | H | |
| 40 | C₃H₇-i | Me | 4-F | H | |
| 41 | C₃H₇-i | Me | H | CO—Me | |
| 42 | C₄H₉-t | Me | H | H | |
| 43 | | | | | |
| 44 | —CH(Me)Et | Me | H | H | 6,42; 6,54 |
| 45 | —CH(Me)Et | Me | 2-F | H | |
| 46 | —CH(Me)Et | Me | 3-F | H | 6,49; 6,52 |
| 47 | —CH(Me)Et | Me | 4-F | H | |
| 48 | —CH(Me)Et | Me | H | SO₂4-Me—Ph | 6,65; 6,73 |
| 49 | —CH(Me)Et | Me | 2-F | SO₂4-Me—Ph | |
| 50 | —CH(Me)Et | Me | 3-F | SO₂4-Me—Ph | |
| 51 | —CH(Me)Et | Me | 4-F | SO₂4-Me—Ph | 6,81(2H) |
| 52 | —CH(Me)Et | Me | H | CO—CH₃ | 6,82; 6,85 |
| 53 | n-Butyl | Me | H | SO₂4-Me—Ph | 6,54; 6,72 |
| 54 | n-Butyl | Me | H | H | 6,45; 6,55 |
| 55 | —CH=CHCH₃ | Me | H | H | |
| 56 | —CH=CHCH₃ | Me | 3-F | H | |
| 57 | —C≡C—Me | Me | H | H | |
| 58 | —C≡C—Me | Me | 2-F | H | |
| 59 | —C≡C—Me | Me | 3-F | H | |
| 60 | —C≡C—Me | Me | 4-F | H | |
| 61 | —C≡C—Me | Me | H | CO—Me | |
| 62 | —C≡C—Me | Me | H | CN | |
| 63 | cyclopropyl-CH₃ | Me | H | H | |

TABLE 1-continued (I)

|  |  |  |  |  |
|---|---|---|---|---|
|  |  |  | Me = methyl |  |
|  |  |  | Ph = phenyl |  |

| No. | R¹ | R² | R⁴ | R³ | ¹H-NMR data (H₁ v. H₂) |
|---|---|---|---|---|---|
| 64 | cyclopropyl-CH₃ | Me | 3-F | H | |
| 65 | —CH₂F | Me | H | H | |
| 66 | —CH₂F | Me | 3-F | H | |
| 67 | —CH₂F | Me | H | CO—CH₃ | |
| 68 | —CH₂Cl | Me | H | H | 6.75; 6.8 |
| 69 | —CH₂Cl | Me | 3-F | H | |
| 70 | —CHCl₂ | Me | H | H | |
| 71 | —CH₂Br | Me | H | H | |
| 72 | —CH₂Br | Me | 3-F | H | |
| 73 | —CH₂OH | Me | H | H | 6.60; 6.65 |
| 74 | —CH₂OH | Me | 2-F | H | |
| 75 | —CH₂OH | Me | 3-F | H | |
| 76 | —CH₂OH | Me | 4-F | H | |
| 77 | —CH₂OH | Me | H | CO—Me | 6.95; 7.3; 4.6(2H; C$\underline{H}_2$—OH) |
| 78 | —CH₂OMe | Me | H | H | |
| 79 | —CH₂OMe | Me | 3-F | H | |
| 80 | —CH₂OMe | Me | H | CO—CH₃ | |
| 81 | —CH₂O—CH₂CH=CH₂ | Me | H | H | |
| 82 | —CH₂O—Et | Me | H | H | |
| 83 | CH₂O—CH₂C≡CH | Me | H | H | |
| 84 | —CH₂O—C₃H₇-n | Me | H | H | |
| 85 | —CH₂O—C₃H₇-i | Me | H | H | |
| 86 | —CH₂O—C₄H₉-n | Me | H | H | |
| 87 | —CH₂O—CH₂CH₂Cl | Me | H | H | |
| 88 | —CH₂O—CH₂CF₃ | Me | H | H | |
| 89 | —CH₂O—CH₂—CH₂OMe | H | H | H | |
| 90 | —CH=O | Me | H | H | 6.95; 7.3; 10.05(1H, —C$\underline{H}$O) |
| 91 | —CH=O | Me | 2-F | H | |
| 92 | —CH=O | Me | 3-F | H | |
| 93 | —CH=O | Me | 4-F | H | |
| 94 | —CH=O | Me | H | CO—CH₃ | 6.95; 7.3; 9.9(1H, —C$\underline{H}$O) |
| 95 | —CN | Me | H | H | 6.8; 7.0 |
| 96 | —CN | Me | 2-F | H | |
| 97 | —CN | Me | 3-F | H | |
| 98 | —CN | Me | 4-F | H | |
| 99 | —CN | Me | H | CO—Me | |
| 100 | —CN | Me | H | CN | |
| 101 | —C=NOH | Me | H | H | 6.8; 7.1 |
| 102 | —C=NOH | Me | 2-F | H | |
| 103 | —C=NOH | Me | 3-F | H | |
| 104 | —C=NOH | Me | 4-F | H | |
| 105 | —C=NOH | Me | H | CO—CH₃ | |
| 106 | —C=NOMe | Me | H | H | 6.8; 7.0 |
| 107 | —C=NOMe | Me | 2-F | H | |
| 108 | —C=NOMe | Me | 3-F | H | |
| 109 | —C=NOMe | Me | 4-F | H | |
| 110 | —C=NOMe | Me | H | CO—Me | 7.2; 7.6 |
| 111 | —C=NOMe | Me | H | CN | |
| 112 | —C=NOCH₂CH₂Cl | Me | H | H | |
| 113 | —C=NOEt | Me | H | H | |
| 114 | —C=NOCH₂Ph | Me | H | H | |
| 115 | —C=NOCH=CH₂ | Me | H | H | |
| 116 | —C=NO—C≡CH | Me | H | H | |
| 117 | —CH=N-cyclopropyl | Me | H | H | |
| 118 | —CH=N-cyclopropyl | Me | 3-F | H | |
| 119 | —CH=N—Me | Me | H | H | |
| 120 | —CH=N—Me | Me | 3-F | H | |
| 121 | CH=N—Et | Me | H | H | |
| 122 | CH=N—Ph | Me | H | H | |
| 123 | CH=N—C₃H₇-n | Me | H | H | |
| 124 | CH=N—CH₂Ph | Me | H | H | |
| 125 | CH₂NH₂ | Me | H | H | |

TABLE 1-continued (I)

$$R^2, H_1, H_2, R^1, N, R^3, R^4$$

Me = methyl
Ph = phenyl

| No. | R¹ | R² | R⁴ | R³ | ¹H-NMR data (H₁ v. H₂) |
|---|---|---|---|---|---|
| 126 | CH₂NH—Me | Me | H | H | |
| 127 | CH₂NH—Et | Me | H | H | |
| 128 | CH₂NH—Ph | Me | H | H | |
| 129 | CH₂NH—CH₂—Ph | Me | H | H | |
| 130 | CH₂NH—C₃H₇-iso | Me | H | H | |
| 131 | CH₂NH-cyclopropyl | Me | H | H | |
| 132 | Cl | Me | H | H | |
| 133 | Cl | Me | 2-F | H | |
| 134 | Cl | Me | 3-F | H | |
| 135 | Cl | Me | 4-F | H | |
| 136 | Cl | Me | H | CO—Me | |
| 137 | Cl | Me | H | CN | |
| 138 | Br | Me | H | H | |
| 139 | Br | Me | 2-F | H | |
| 140 | Br | Me | 3-F | H | |
| 141 | Br | Me | 4-F | H | |
| 142 | Br | Me | H | CO—Me | |
| 143 | Br | Me | H | CN | |
| 144 | F | Me | H | H | |
| 145 | I | Me | H | H | |
| 146 | OMe | Me | H | H | |
| 147 | OMe | Me | 2-F | H | |
| 148 | OMe | Me | 3-F | H | |
| 149 | OMe | Me | 4-F | H | |
| 150 | OMe | Me | H | CO—Me | |
| 151 | OMe | Me | H | CN | |
| 152 | OEt | Me | H | H | |
| 153 | OEt | Me | 3-F | H | |
| 154 | O—C₃H₇-i | Me | H | H | |
| 155 | O—C₃H₇-i | Me | 3-F | H | |
| 156 | O—C₃H₇-n | Me | H | H | |
| 157 | O—C₃H₇-n | Me | 3-F | H | |
| 158 | Me | Ethyl | H | H | |
| 159 | Me | Ethyl | 2-F | H | |
| 160 | Me | Ethyl | 3-F | H | |
| 161 | Me | Ethyl | 4-F | H | |
| 162 | Me | Ethyl | H | CO—Me | |
| 163 | Me | Ethyl | H | CN | |
| 164 | Cyclopropyl | Ethyl | H | H | |
| 165 | Cyclopropyl | Ethyl | 2-F | H | |
| 166 | Cyclopropyl | Ethyl | 3-F | H | |
| 167 | Cyclopropyl | Ethyl | 4-F | H | |
| 168 | Cyclopropyl | Ethyl | H | CO—Me | |
| 169 | Cyclopropyl | Ethyl | H | CN | |
| 170 | —C(Me)ethyl | Ethyl | H | H | |
| 171 | —C(Me)ethyl | Ethyl | 2-F | H | |
| 172 | —C(Me)ethyl | Ethyl | 3-F | H | |
| 173 | —C(Me)ethyl | Ethyl | 4-F | H | |
| 174 | —C(Me)ethyl | Ethyl | H | CO—Me | |
| 175 | —C(Me)ethyl | Ethyl | H | CN | |
| 176 | -Ethyl | Ethyl | H | H | |
| 177 | -Ethyl | Ethyl | 3-F | H | |
| 178 | C₃H₇-i | Ethyl | H | H | |
| 179 | C₃H₇-i | Ethyl | 3-F | H | |
| 180 | n-Butyl | Ethyl | H | H | |
| 181 | n-Butyl | Ethyl | 3-F | H | |
| 182 | CF₃ | Ethyl | H | H | |
| 183 | CF₃ | Ethyl | 3-F | H | |
| 184 | —C≡C—Me | Ethyl | H | H | |
| 185 | —C≡C—Me | Ethyl | 3-F | H | |
| 186 | cyclopropyl-CH₃ | Ethyl | H | H | |
| 187 | —CH₂Cl | Ethyl | H | H | |

TABLE 1-continued

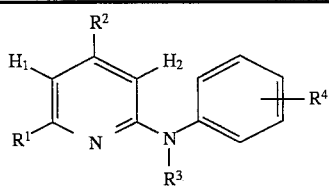

Me = methyl
Ph = phenyl

| No. | R¹ | R² | R⁴ | R³ | ¹H-NMR data (H₁ v. H₂) |
|---|---|---|---|---|---|
| 188 | —CH₂Cl | Ethyl | 3-F | H | |
| 189 | —CH₂Br | Ethyl | H | H | |
| 190 | —CH₂Br | Ethyl | 3-F | H | |
| 191 | —CH₂OMe | Ethyl | H | H | |
| 192 | —CH₂OMe | Ethyl | 3-F | H | |
| 193 | —CH=O | Ethyl | H | H | |
| 194 | —CH=O | Ethyl | 2-F | H | |
| 195 | —CH=O | Ethyl | 3-F | H | |
| 196 | —CH=O | Ethyl | 4-F | H | |
| 197 | —CN | Ethyl | H | H | |
| 198 | —CN | Ethyl | 2-F | H | |
| 199 | —CN | Ethyl | 3-F | H | |
| 200 | —CN | Ethyl | 4-F | H | |
| 201 | —CN | Ethyl | H | CO—Me | |
| 202 | —CN | Ethyl | H | CN | |
| 203 | —C=NOH | Ethyl | H | H | |
| 204 | —C=NOH | Ethyl | 3-F | H | |
| 205 | —C=NOMe | Ethyl | H | H | |
| 206 | —C=NOMe | Ethyl | 2-F | H | |
| 207 | —C=NOMe | Ethyl | 3-F | H | |
| 208 | —C=NOMe | Ethyl | 4-F | H | |
| 209 | —C=NOMe | Ethyl | H | CO—Me | |
| 210 | —C=NOMe | Ethyl | H | CN | |
| 211 | —C=NOCH₂CH₂Cl | Ethyl | H | H | |
| 212 | —C=NOEt | Ethyl | H | H | |
| 213 | —C=NOCH₂Ph | Ethyl | H | H | |
| 214 | —C=NOCH=CH₂ | Ethyl | H | H | |
| 215 | —C=NO—C≡C—H | Ethyl | H | H | |
| 216 | —CH=N-cyclopropyl | Ethyl | H | H | |
| 217 | —CH=N-cyclopropyl | Ethyl | 3-F | H | |
| 218 | —CH=N—Me | Ethyl | H | H | |
| 219 | —CH=N—Me | Ethyl | 3-F | H | |
| 220 | CH=N-Ethyl | Ethyl | H | H | |
| 221 | CH=N—Ph | Ethyl | H | H | |
| 222 | CH=N—C₃H₇-n | Ethyl | H | H | |
| 223 | CH=N—CH₂Ph | Ethyl | H | H | |
| 224 | CH₂NH₂ | Ethyl | H | H | |
| 225 | CH₂NH—Me | Ethyl | H | H | |
| 226 | CH₂NH-ethyl | Ethyl | H | H | |
| 227 | CH₂NH—Ph | Ethyl | H | H | |
| 228 | CH₂NH—CH₂—PH | Ethyl | H | H | |
| 229 | CH₂NH—C₃H₇-iso | Ethyl | H | H | |
| 230 | CH₂NH-cyclopropyl | Ethyl | H | H | |
| 231 | Cl | Ethyl | H | H | |
| 232 | Cl | Ethyl | 2-F | H | |
| 233 | Cl | Ethyl | 3-F | H | |
| 234 | Cl | Ethyl | 4-F | H | |
| 235 | Cl | Ethyl | H | CO—Me | |
| 236 | Cl | Ethyl | H | CN | |
| 237 | Br | Ethyl | H | H | |
| 238 | Br | Ethyl | 2-F | H | |
| 239 | Br | Ethyl | 3-F | H | |
| 240 | Br | Ethyl | 4-F | H | |
| 241 | Br | Ethyl | H | CO—Me | |
| 242 | Br | Ethyl | H | CN | |
| 243 | OMe | Ethyl | H | H | |
| 244 | OMe | Ethyl | 2-F | H | |
| 245 | OMe | Ethyl | 3-F | H | |
| 246 | OMe | Ethyl | 4-F | H | |
| 247 | OMe | Ethyl | H | CO—Me | |
| 248 | OMe | Ethyl | H | CN | |
| 249 | OEt | Ethyl | H | H | |
| 250 | OEt | Ethyl | 3-F | H | |
| 251 | Me | Isopropyl | H | H | |
| 252 | Me | Isopropyl | 2-F | H | |
| 253 | Me | Isopropyl | 3-F | H | |
| 254 | Me | Isopropyl | 4-F | H | |

TABLE 1-continued

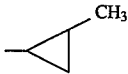

(I)

Me = methyl
Ph = phenyl

| No. | R¹ | R² | R⁴ | R³ | ¹H-NMR data (H₁ v. H₂) |
|---|---|---|---|---|---|
| 255 | Me | Isopropyl | H | CO—Me | |
| 256 | Me | Isopropyl | H | CN | |
| 257 | Cyclopropyl | Isopropyl | H | H | |
| 258 | Cyclopropyl | Isopropyl | 2-F | H | |
| 259 | Cyclopropyl | Isopropyl | 3-F | H | |
| 260 | Cyclopropyl | Isopropyl | 4-F | H | |
| 261 | Cyclopropyl | Isopropyl | H | CO—Me | |
| 262 | Cyclopropyl | Isopropyl | H | CN | |
| 263 | —C(Me)ethyl | Isopropyl | H | H | |
| 264 | —C(Me)ethyl | Isopropyl | 2-F | H | |
| 265 | —C(Me)ethyl | Isopropyl | 3-F | H | |
| 266 | —C(Me)ethyl | Isopropyl | 4-F | H | |
| 267 | —C(Me)ethyl | Isopropyl | H | CO—Me | |
| 268 | —C(Me)ethyl | Isopropyl | H | CN | |
| 269 | -Ethyl | Isopropyl | H | H | |
| 270 | -Ethyl | Isopropyl | 3-F | H | |
| 271 | n-Butyl | Isopropyl | H | H | |
| 272 | n-Butyl | Isopropyl | 3-F | H | |
| 273 | ▷—CH₃ | Isopropyl | H | H | |
| 274 | —CH₂Cl | Isopropyl | H | H | |
| 275 | —CH₂Cl | Isopropyl | 3-F | H | |
| 276 | —CH₂Br | Isopropyl | H | H | |
| 277 | —CH₂Br | Isopropyl | 3-F | H | |
| 278 | —CH₂OMe | Isopropyl | H | H | |
| 279 | —CH₂OMe | Isopropyl | 3-F | H | |
| 280 | —CH=O | Isopropyl | H | H | |
| 281 | —CH=O | Isopropyl | 2-F | H | |
| 282 | —CH=O | Isopropyl | 3-F | H | |
| 283 | —CH=O | Isopropyl | 4-F | H | |
| 284 | —CN | Isopropyl | H | H | |
| 285 | —CN | Isopropyl | 2-F | H | |
| 286 | —CN | Isopropyl | 3-F | H | |
| 287 | —CN | Isopropyl | 4-F | H | |
| 288 | —CN | Isopropyl | H | CO—Me | |
| 289 | —CN | Isopropyl | H | CN | |
| 290 | —C=NOH | Isopropyl | H | H | |
| 291 | —C=NOH | Isopropyl | 3-F | H | |
| 292 | —C=NOMe | Isopropyl | H | H | |
| 293 | —C=NOMe | Isopropyl | 2-F | H | |
| 294 | —C=NOMe | Isopropyl | 3-F | H | |
| 295 | —C=NOMe | Isopropyl | 4-F | H | |
| 296 | —C=NOMe | Isopropyl | H | CO—Me | |
| 297 | —C=NOMe | Isopropyl | H | CN | |
| 298 | —C=NOCH₂CH₂Cl | Isopropyl | H | H | |
| 299 | —C=NOEt | Isopropyl | H | H | |
| 300 | —C=NOCH₂Ph | Isopropyl | H | H | |
| 301 | —C=NOCH=CH₂ | Isopropyl | H | H | |
| 302 | —C=NO—C≡CH | Isopropyl | H | H | |
| 303 | —CH=N-cyclopropyl | Isopropyl | H | H | |
| 304 | —CH=N-cyclopropyl | Isopropyl | 3-F | H | |
| 305 | —CH=N—Me | Isopropyl | H | H | |
| 306 | —CH=N—Me | Isopropyl | 3-F | H | |
| 307 | CH=N-isopropyl | Isopropyl | H | H | |
| 308 | CH=N—Ph | Isopropyl | H | H | |
| 309 | CH=N—C₃H₇-n | Isopropyl | H | H | |
| 310 | CH=N—CH₂Ph | Isopropyl | H | H | |
| 311 | CH₂NH₂ | Isopropyl | H | H | |
| 312 | CH₂NH—Me | Isopropyl | H | H | |
| 313 | CH₂NH-isopropyl | Isopropyl | H | H | |
| 314 | CH₂NH—Ph | Isopropyl | H | H | |
| 315 | CH₂NH—CH₂—Ph | Isopropyl | H | H | |
| 316 | CH₂NH—C₃H₇-iso | Isopropyl | H | H | |
| 317 | CH₂NH-cyclopropyl | Isopropyl | H | H | |

5,569,765

TABLE 1-continued (I)

Structure: pyridine with R¹ at position 6, R² at position 4, H₁ at position 5, H₂ at position 3, and at position 2 an N(R³) linked to a phenyl bearing R⁴.

Me = methyl
Ph = phenyl

| No. | R¹ | R² | R⁴ | R³ | ¹H-NMR data (H₁ v. H₂) |
|---|---|---|---|---|---|
| 318 | Cl | Isopropyl | H | H | |
| 319 | Cl | Isopropyl | 2-F | H | |
| 320 | Cl | Isopropyl | 3-F | H | |
| 321 | Cl | Isopropyl | 4-F | H | |
| 322 | Cl | Isopropyl | H | CO—Me | |
| 323 | Cl | Isopropyl | H | CN | |
| 324 | Br | Isopropyl | H | H | |
| 325 | Br | Isopropyl | 2-F | H | |
| 326 | Br | Isopropyl | 3-F | H | |
| 327 | Br | Isopropyl | 4-F | H | |
| 328 | Br | Isopropyl | H | CO—Me | |
| 329 | Br | Isopropyl | H | CN | |
| 330 | OMe | Isopropyl | H | H | |
| 331 | OMe | Isopropyl | 2-F | H | |
| 332 | OMe | Isopropyl | 3-F | H | |
| 333 | OMe | Isopropyl | 4-F | H | |
| 334 | OMe | Isopropyl | H | CO—Me | |
| 335 | OMe | Isopropyl | H | CN | |
| 336 | OEt | Isopropyl | H | H | |
| 337 | OEt | Isopropyl | 3-F | H | |
| 338 | Me | Cyclopropyl | H | H | 6.3; 6.55 |
| 339 | Me | Cyclopropyl | 2-F | H | |
| 340 | Me | Cyclopropyl | 3-F | H | |
| 341 | Me | Cyclopropyl | 4-F | H | |
| 342 | Me | Cyclopropyl | H | CO—Me | |
| 343 | Me | Cyclopropyl | H | CN | |
| 344 | Ethyl | Cyclopropyl | H | H | |
| 345 | Ethyl | Cyclopropyl | 3-F | H | |
| 346 | Cyclopropyl | Cyclopropyl | H | H | 6.35; 6.4 |
| 347 | Cyclopropyl | Cyclopropyl | 2-F | H | |
| 348 | Cyclopropyl | Cyclopropyl | 3-F | H | |
| 349 | Cyclopropyl | Cyclopropyl | 4-F | H | |
| 350 | Cyclopropyl | Cyclopropyl | H | CO—Me | |
| 351 | Cyclopropyl | Cyclopropyl | H | CN | |
| 352 | —C(Me)Et | Cyclopropyl | H | H | |
| 353 | —C(Me)Et | Cyclopropyl | 2-F | H | |
| 354 | —C(Me)Et | Cyclopropyl | 3-F | H | |
| 355 | —C(Me)Et | Cyclopropyl | 4-F | H | |
| 356 | —C(Me)Et | Cyclopropyl | H | CO—Me | |
| 357 | —C(Me)Et | Cyclopropyl | H | CN | |
| 358 | n-Butyl | Cyclopropyl | H | H | |
| 359 | n-Butyl | Cyclopropyl | 3-F | H | |
| 360 | CF₃ | Cyclopropyl | H | H | |
| 361 | CF₃ | Cyclopropyl | 3-F | H | |
| 362 | —C≡C—Me | Cyclopropyl | H | H | |
| 363 | —C≡C—Me | Cyclopropy | 3-F | H | |
| 364 | C₃H₇-i | Cyclopropyl | H | H | |
| 365 | C₃H₇-i | Cyclopropyl | 3-F | H | |
| 366 | cyclopropyl | Cyclopropyl | 3-F | H | |
| 367 | methylcyclopropyl | Cyclopropyl | H | H | |
| 368 | —CH₂Cl | Cyclopropyl | H | H | |
| 369 | —CH₂Cl | Cyclopropyl | 3-F | H | |
| 370 | —CH₂Br | Cyclopropyl | H | H | |
| 371 | —CH₂Br | Cyclopropyl | 3-F | H | |
| 372 | —CH₂OMe | Cyclopropyl | H | H | |
| 373 | —CH₂OMe | Cyclopropyl | 3-F | H | |
| 374 | —CH=O | Cyclopropyl | H | H | |
| 375 | —CH=O | Cyclopropyl | 2-F | H | |
| 376 | —CH=O | Cyclopropyl | 3-F | H | |

TABLE 1-continued (I)

Me = methyl
Ph = phenyl

| No. | R¹ | R² | R⁴ | R³ | ¹H-NMR data (H₁ v. H₂) |
|---|---|---|---|---|---|
| 377 | —CH=O | Cyclopropyl | 4-F | H | |
| 378 | —CN | Cyclopropyl | H | H | |
| 379 | —CN | Cyclopropyl | 2-F | H | |
| 380 | —CN | Cyclopropyl | 3-F | H | |
| 381 | —CN | Cyclopropyl | 4-F | H | |
| 382 | —CN | Cyclopropyl | H | CO—Me | |
| 383 | —CN | Cyclopropyl | H | CN | |
| 384 | —C=NOH | Cyclopropyl | H | H | |
| 385 | —C=NOH | Cyclopropyl | 3-F | H | |
| 386 | —C=NOMe | Cyclopropyl | H | H | |
| 387 | —C=NOMe | Cyclopropyl | 2-F | H | |
| 388 | —C=NOMe | Cyclopropyl | 3-F | H | |
| 389 | —C=NOMe | Cyclopropyl | 4-F | H | |
| 389 | —C=NOMe | Cyclopropyl | H | CO—Me | |
| 390 | —C=NOMe | Cyclopropyl | H | CN | |
| 391 | —C=NOCH₂CH₂Cl | Cyclopropyl | H | H | |
| 392 | —C=NOEt | Cyclopropyl | H | H | |
| 393 | —C=NOCH₂Ph | Cyclopropyl | H | H | |
| 394 | —C=NOCH=CH₂ | Cyclopropyl | H | H | |
| 395 | —C=NO—C≡C—H | Cyclopropyl | H | H | |
| 396 | —CH=N-cyclopropyl | Cyclopropyl | H | H | |
| 397 | —CH=N-cyclopropyl | Cyclopropyl | 3-F | H | |
| 398 | —CH=N—Me | Cyclopropyl | H | H | |
| 399 | —CH=N—Me | Cyclopropyl | 3-F | H | |
| 400 | CH=N—Et | Cyclopropyl | H | H | |
| 401 | CH=N—Ph | Cyclopropyl | H | H | |
| 402 | CH=N—C₃H₇-n | Cyclopropyl | H | H | |
| 403 | CH=N—CH₂Ph | Cyclopropyl | H | H | |
| 404 | CH₂NH₂ | Cyclopropyl | H | H | |
| 405 | CH₂NH—Me | Cyclopropyl | H | H | |
| 406 | CH₂NH—Et | Cyclopropyl | H | H | |
| 407 | CH₂NH—Ph | Cyclopropyl | H | H | |
| 408 | CH₂NH—CH₂—Ph | Cyclopropyl | H | H | |
| 409 | CH₂NH—C₃H₇-iso | Cyclopropyl | H | H | |
| 410 | CH₂NH-cyclopropyl | Cyclopropyl | H | H | |
| 411 | Cl | Cyclopropyl | H | H | |
| 412 | Cl | Cyclopropyl | 2-F | H | |
| 413 | Cl | Cyclopropyl | 3-F | H | |
| 414 | Cl | Cyclopropyl | 4-F | H | |
| 415 | Cl | Cyclopropyl | H | CO—Me | |
| 416 | Cl | Cyclopropyl | H | CN | |
| 417 | Br | Cyclopropyl | H | H | |
| 418 | Br | Cyclopropyl | 2-F | H | |
| 419 | Br | Cyclopropyl | 3-F | H | |
| 420 | Br | Cyclopropyl | 4-F | H | |
| 421 | Br | Cyclopropyl | H | CO—Me | |
| 422 | Br | Cyclopropyl | H | CN | |
| 423 | OMe | Cyclopropyl | H | H | |
| 424 | OMe | Cyclopropyl | 2-F | H | |
| 425 | OMe | Cyclopropyl | 3-F | H | |
| 426 | OMe | Cyclopropyl | 4-F | H | |
| 427 | OMe | Cyclopropyl | H | CO—Me | |
| 428 | OMe | Cyclopropyl | H | CN | |
| 429 | OEt | Cyclopropyl | H | H | |
| 430 | OEt | Cyclopropyl | 3-F | H | |
| 431 | Me | —C≡C—Me | H | H | |
| 432 | Me | —C≡C—Me | 2-F | H | |
| 433 | Me | —C≡C—Me | 3-F | H | |
| 434 | Me | —C≡C—Me | 4-F | H | |
| 435 | Me | —C≡C—Me | H | CO—Me | |
| 436 | Me | —C≡C—Me | H | CN | |

TABLE 1-continued (I)

| No. | R¹ | R² | R⁴ | R³ | ¹H-NMR data (H₁ v. H₂) |
|---|---|---|---|---|---|
| 437 | Ethyl | —C≡C—Me | H | H | |
| 438 | Ethyl | —C≡C—Me | 3-F | H | |
| 439 | C₃H₇-i | —C≡C—Me | H | H | |
| 440 | C₃H₇-i | —C≡C—Me | 3-F | H | |
| 441 | Cyclopropyl | —C≡C—Me | H | H | |
| 442 | Cyclopropyl | —C≡C—Me | 2-F | H | |
| 443 | Cyclopropyl | —C≡C—Me | 3-F | H | |
| 444 | Cyclopropyl | —C≡C—Me | 4-F | H | |
| 445 | Cyclopropyl | —C≡C—Me | H | CO—Me | |
| 446 | Cyclopropyl | —C≡C—Me | H | CN | |
| 447 | —C(Me)Et | —C≡C—Me | H | H | |
| 448 | —C(Me)Et | —C≡C—Me | 2-F | H | |
| 449 | —C(Me)Et | —C≡C—Me | 3-F | H | |
| 450 | —C(Me)Et | —C≡C—Me | 4-F | H | |
| 451 | —C(Me)Et | —C≡C—Me | H | CO—Me | |
| 452 | —C(Me)Et | —C≡C—Me | H | CN | |
| 453 | n-Butyl | —C≡C—Me | H | H | |
| 454 | n-Butyl | —C≡C—Me | 3-F | H | |
| 455 | CF₃ | —C≡C—Me | H | H | |
| 456 | CF₃ | —C≡C—Me | 3-F | H | |
| 457 | cyclopropyl-CH₃ | —C≡C—Me | H | H | |
| 458 | cyclopropyl-CH₃ | —C≡C—Me | 3-F | H | |
| 459 | —CH₂Cl | —C≡C—Me | H | H | |
| 460 | —CH₂Cl | —C≡C—Me | 3-F | H | |
| 470 | —CH₂Br | —C≡C—Me | H | H | |
| 471 | —CH₂Br | —C≡C—Me | 3-F | H | |
| 472 | —CH₂OMe | —C≡C—Me | H | H | |
| 473 | —CH₂OMe | —C≡C—Me | 3-F | H | |
| 474 | —CH=O | —C≡C—Me | H | H | |
| 475 | —CH=O | —C≡C—Me | 2-F | H | |
| 476 | —CH=O | —C≡C—Me | 3-F | H | |
| 477 | —CH=O | —C≡C—Me | 4-F | H | |
| 478 | —CN | —C≡C—Me | H | H | |

Me = methyl
Ph = phenyl

TABLE 1-continued

Structure (I): Pyridine with R¹ at position 6, H₁ at position 5, R² at position 4, H₂ at position 3, and at position 2 an N(R³) linked to a phenyl bearing R⁴.

Me = methyl
Ph = phenyl

| No. | R¹ | R² | R⁴ | R³ | ¹H-NMR data (H₁ v. H₂) |
|---|---|---|---|---|---|
| 479 | —CN | —C≡C—Me | 2-F | H | |
| 480 | —CN | —C≡C—Me | 3-F | H | |
| 481 | —CN | —C≡C—Me | 4-F | H | |
| 482 | —CN | —C≡C—Me | H | CO—Me | |
| 483 | —CN | —C≡C—Me | H | CN | |
| 484 | —C=NOH | —C≡C—Me | H | H | |
| 485 | —C=NOH | —C≡C—Me | 3-F | H | |
| 486 | —C=NOMe | —C≡C—Me | H | H | |
| 487 | —C=NOMe | —C≡C—Me | 2-F | H | |
| 488 | —C=NOMe | —C≡C—Me | 3-F | H | |
| 489 | —C=NOMe | —C≡C—Me | 4-F | H | |
| 490 | —C=NOMe | —C≡C—Me | H | CO—Me | |
| 491 | —C=NOMe | —C≡C—Me | H | CN | |
| 492 | —C=NOCH₂CH₂Cl | —C≡C—Me | H | H | |
| 493 | —C=NOEt | —C≡C—Me | H | H | |
| 494 | —C=NOCH₂Ph | —C≡C—Me | H | H | |
| 495 | —C=NOCH=CH₂ | —C≡C—Me | H | H | |
| 496 | —C=NO—C≡CH | —C≡C—Me | H | H | |
| 497 | —CH=N-cyclopropyl | —C≡C—Me | H | H | |
| 498 | —CH=N-cyclopropyl | —C≡C—Me | 3-F | H | |
| 499 | —CH=N—Me | —C≡C—Me | H | H | |
| 500 | —CH=N—Me | —C≡C—Me | 3-F | H | |
| 501 | —CH=N—Et | —C≡C—Me | H | H | |
| 502 | —CH=N—Ph | —C≡C—Me | H | H | |
| 503 | —CH=N—C₃H₇-n | —C≡C—Me | H | H | |
| 504 | —CH=N—CH₂Ph | —C≡C—Me | H | H | |
| 505 | —CH₂NH₂ | —C≡C—Me | H | H | |
| 506 | —CH₂NH—Me | —C≡C—Me | H | H | |
| 507 | —CH₂NH—Et | —C≡C—Me | H | H | |
| 508 | —CH₂NH—Ph | —C≡C—Me | H | H | |
| 509 | —CH₂NH—CH₂—PH | —C≡C—Me | H | H | |
| 510 | —CH₂NH—C₃H₇-iso | —C≡C—Me | H | H | |
| 511 | —CH₂NH-cyclopropyl | —C≡C—Me | H | H | |
| 512 | Cl | —C≡C—Me | H | H | |
| 513 | Cl | —C≡C—Me | 2-F | H | |
| 514 | Cl | —C≡C—Me | 3-F | H | |
| 515 | Cl | —C≡C—Me | 4-F | H | |

TABLE 1-continued $$\text{(I)}$$

Structure: pyridine with $H_1$, $R^2$, $H_2$, $R^1$, N, and N($R^3$)-phenyl-$R^4$ substituents.

Me = methyl
Ph = phenyl

| No. | R¹ | R² | R⁴ | R³ | ¹H-NMR data (H₁ v. H₂) |
|---|---|---|---|---|---|
| 516 | Cl | —C≡C—Me | H | CO—Me | |
| 517 | Cl | —C≡C—Me | H | CN | |
| 518 | Br | —C≡C—Me | H | H | |
| 519 | Br | —C≡C—Me | 2-F | H | |
| 520 | Br | —C≡C—Me | 3-F | H | |
| 521 | Br | —C≡C—Me | 4-F | H | |
| 522 | Br | —C≡C—Me | H | CO—Me | |
| 523 | Br | —C≡C—Me | H | CN | |
| 524 | OMe | —C≡C—Me | H | H | |
| 525 | OMe | —C≡C—Me | 2-F | H | |
| 526 | OMe | —C≡C—Me | 3-F | H | |
| 527 | OMe | —C≡C—Me | 4-F | H | |
| 528 | OMe | —C≡C—Me | H | CO—Me | |
| 529 | OMe | —C≡C—Me | H | CN | |
| 530 | OEt | —C≡C—Me | H | H | |
| 531 | OEt | —C≡C—Me | 3-F | H | |
| 532 | Me | Me | H | H | |
| 533 | Cyclopropyl | Me | 3-F | CO—Me | 6.45; 6.6 |
| 534 | C(CH₃)Et | Me | 3-F | CO—Me | 6.65; 6.7 |
| 535 | n-Butyl | Me | H | CO—Me | 6.7(2H) |

The compounds of the formula I are suitable as fungicides.

The fungicidal compounds or the compositions containing them can be used, for example, in the form of directly sprayable solutions, powders, suspensions, also high percentage aqueous, oily or other suspensions or dispersions, emulsions, oil dispersions, pastes, dusting compositions, scattering compositions or granules by spraying, atomizing, dusting, scattering or watering. The application forms depend on the intended uses; they should in each case if possible guarantee the finest dispersion of the active compounds according to the invention.

Normally, the plants are sprayed or dusted with the active compounds or the seeds of the plants are treated with the active compounds.

The formulations are prepared in known manner, eg. by extending the active compound with solvents and/or carriers, if desired using emulsifiers and dispersants, it also being possible to use other organic solvents as auxiliary solvents when water is used as a diluent. Suitable auxiliaries for this purpose are essentially: solvents such as aromatics (eg. xylene), chlorinated aromatics (eg. chlorobenzenes), paraffins (eg. mineral oil fractions), alcohols (eg. methanol or butanol), ketones (eg. cyclohexanone), amines (eg. ethanolamine or dimethylformamide) and water; carriers such as ground natural minerals (eg. kaolins, clays, talc or chalk) and ground synthetic minerals (eg. highly disperse silicic acid or silicates); emulsifiers such as nonionic and anionic emulsifiers (eg. polyoxyethylene fatty alcohol ethers, alkylsulfonates and arylsulfonates) and dispersants such as lignin sulfite waste liquors and methylcellulose.

Suitable surface-active substances are the alkali metal, alkaline earth metal or ammonium salts of aromatic sulfonic acids, eg. lignosulfonic acid, phenolsulfonic acid, naphthalenesulfonic acid and dibutylnaphthalenesulfonic acid, as well as of fatty acids, alkyl- and alkylarylsulfonates, alkyl, lauryl ether and fatty alcohol sulfates, and also salts of sulfated hexa-, hepta- and octadecanols, as well as of fatty alcohol glycol ethers, condensation products of sulfonated naphthalene and its derivatives with formaldehyde, condensation products of naphthalene or of naphthalenesulfonic acids with phenol and formaldehyde, polyoxyethylene octyl phenol ether, ethoxylated isooctyl-, octyl- or nonylphenol, alkylphenol or tributylphenyl polyglycol ethers, alkylaryl polyether alcohols, isotridecyl alcohol, fatty alcohol-ethylene oxide condensates, ethoxylated castor oil, polyoxyethylene alkyl ethers or polyoxypropylene, lauryl alcohol polyglycol ether acetate, sorbitol esters, lignin-sulfite waste liquors or methylcellulose.

Powder, scattering and dusting compositions can be prepared by mixing or joint grinding of the active substances with a solid carrier.

Granules, eg. coated, impregnated and homogeneous granules can be prepared by binding the active compounds to solid carriers. Solid carriers are mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground plastics, fertilizers, such as ammonium sulfate, ammonium phosphate, ammonium nitrate, ureas and vegetable products, such as cereal meal, tree bark, wood and nutshell meal, cellulose powder or other solid carriers.

Examples of such preparations are:

I. a solution of 90 parts by weight of compound 7 and 10 parts by weight of N-methyl-α-pyrrolidone, which is suitable for application in the form of very small drops;

II. a mixture of 20 parts by weight of compound 24, 80 parts by weight of xylene, 10 parts by weight of the addition product of 8 to 10 mol of ethylene oxide to 1 mol of oleic acid N-monoethanolamide, 5 parts by weight of calcium salt of dodecylbenzenesulfonic acid, 5 parts by weight of the addition product of 40 mol of ethylene oxide to 1 mol of castor oil; a dispersion is obtained by fine dispersion of the solution in water.

III. an aqueous dispersion of 20 parts by weight of compound 25, 40 parts by weight of cyclohexanone, 30 parts by weight of isobutanol, 20 parts by weight of the addition product of 40 mol of ethylene oxide to 1 mol of castor oil;

IV. an aqueous dispersion of 20 parts by weight of compound 7, 25 parts by weight of cyclohexanol, 65 parts by weight of a mineral oil fraction of boiling point 210° to 280° C. and 10 parts by weight of the addition product of 40 mol of ethylene oxide to 1 mol of castor oil;

V. a mixture ground in a hammer mill, composed of 80 parts by weight of compound 24, 3 parts by weight of the sodium salt of diisobutylnaphthalene-α-sulfonic acid, 10 parts by weight of the sodium salt of a lignosulfonic acid from a sulfite waste liquor and 7 parts by weight of powdered silica gel; a spray liquor is obtained by fine dispersion of the mixture in water;

VI. an intimate mixture of 3 parts by weight of compound 28 and 97 parts by weight of finely divided kaolin; this dusting composition contains 3% by weight of active compound;

VII. an intimate mixture of 30 parts by weight of compound 7, 92 parts by weight of powdered silica gel and 8 parts by weight of paraffin oil which has been sprayed onto the surface of this silica gel; this preparation gives the active compound a good adhesion;

VIII. a stable aqueous dispersion of 40 parts by weight of compound 24, 10 parts by weight of the sodium salt of a phenolsulfonic acid-urea-formaldehyde condensate, 2 parts by weight of silica gel and 48 parts by weight of water, which can be further diluted;

IX. a stable oily aispersion of 20 parts by weight of compound 28, 2 parts by weight of the calcium salt of dodecylbenzenesulfonic acid, 8 parts by weight of fatty alcohol polyglycol ether, 20 parts by weight of the sodium salt of a phenolsulfonic acid-urea-formaldehyde condensate and 68 parts by weight of a paraffinic mineral oil.

The compounds of the formula I are distinguished by an outstanding activity against a broad spectrum of phytopathogenic fungi, in particular from the Ascomycetes and Basidiomycetes class. In some cases they are systemically active and can be employed as foliar and soil fungicides.

They are of particular importance for the control of a multiplicity of fungi on various crop plants such as wheat, rye, barley, oats, rice, maize, grass, cotton, soybean, coffee, sugar cane, grapes, fruit and decorative plants and vegetable plants such as cucumbers, beans and Cucurbitaceae, as well as on the seeds of these plants.

The compounds are applied by treating the fungi or the seeds, plants, materials or the soil to be protected from fungal attack with a fungicidally effective amount of the active compounds.

Application takes place before or after the infection of the materials, plants or seeds by the fungi.

The compounds I are specifically suitable for the control of the following plant diseases:

*Erysiphe graminis* (powdery mildew) in cereals,

*Erysiphe cichoracearum* and *Sphaerotheca fuliginea* on Cucurbitaceae,

*Podosphaera leucotricha* on apples,

*Uncinula necator* on vines,

Puccinia species on cereals,

Rhizoctonia species on cotton and grass,

Ustilago species on cereals and sugar cane,

*Venturia inaequalis* (scab) on apples,

Helminthosporium species on cereals,

*Septoria nodorum* on wheat,

*Botrytis cinerea* (gray mold) on strawberries, vines,

*Cercospora arachidicola* on groundnuts,

*Pseudocercosporella herpotrichoides* on wheat, barley,

*Pyricularia oryzae* on rice,

*Phytophthora infestans* on potatoes and tomatoes,

Fusarium and Verticillium species on various plants,

*Plasmopara viticola* on vines,

Alternaria species on vegetables and fruit.

The novel compounds can also be employed in the protection of materials (wood preservation), eg. against *Paecilomyces variotii*.

The fungicidal compositions in general contain from 0.1 to 95, preferably from 0.5 to 90, % by weight of active compound.

Depending on the type of effect desired, the application rates are from 0.02 to 3 kg of active compound per ha.

In the case of seed treatment, amounts of active compound from 0.001 to 50 g, preferably 0.01 to 10 g, per kilogram of seed are generally required.

The compositions according to the invention can also be present in the application form as fungicides together with other active compounds, or eg. with herbicides, insecticides, growth regulators, fungicides or alternatively with fertilizers.

On mixing with fungicides, an increase in the spectrum of fungicidal action is obtained here in many cases.

The following list of fungicides, with which the compounds according to the invention can be applied together, is intended to illustrate the combination possibilities but not to restrict them:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate),
zinc (N,N'-propylenebisdithiocarbamate),
N,N-polypropylenebis(thiocarbamoyl) disulfide;

nitro derivates, such as
dinitro(1-methylheptyl)phenyl crotonate,
2-sec-butyl-4,6-dinitrophenyl 3,3-dimethylacrylate,
2-sec-butyl-4,6-dinitrophenyl isopropylcarbonate,
diisopropyl 5-nitroisophthalate;

heterocyclic substances, such as
2-heptadecyl-2-imidazoline acetate,
2,4-dichloro-6-(o-chloroanilino)-s-triazine,
O,O-diethyl phthalimidophosphonothioate,
5-amino-1-[bis-(dimethylamino)phosphinYl]-3-phenyl-1,2,4-triazole,
2,3-dicyano-1,4-dithioanthraquinone,
2-thio-l,3-dithiolo-[4,5-b]quinoxaline,
methyl 1-(butylcarbamoyl)-2-benzimidazolecarbamate,
2-methoxycarbonylaminobenzimidazole,
2-(2-furyl)benzimidazole,
2-(4-thiazolyl)benzimidazole,
N-(1,1,2,2-tetrachloroethylthio)tetrahydrophthalimide,
N-trichloromethylthiotetrahydrophthalimide,
N-trichloromethylthiophthalimide, N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine-1-oxide,
8-hydroxyquinoline or its copper salt,
2,3-dihydro-5-carboxanilido-6-methyl-1,4-oxathiin,
2,3-dihydro-5-carboxanilido-6-methyl-1,4-oxathiin-4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethylfuran-3-carboxycyclohexylamide,
N-cyclohexyl-N-methoxy-2,5-dimethyl-furan-3-carboxamide,
2-methylbenzanilide,
2-iodobenzanilide,
N-formyl-N-morpholine-2,2,2-trichloroethyl acetal,
piperazine-1,4-diylbis(1-(2,2,2-trichloroethyl))formamide,
1-(3,4-dichloroanilino)-1-formylamino-2,2,2-trichloroethane,
2,6-dimethyl-N-tridecylmorpholine or its salts,
2,6-dimethyl-N-cyclododecylmorpholine or its salts,
N-[3-(p-tert-butylphenyl)-2-methylpropyl]-cis-2,6-dimethylmorpholine,
N-[3-(p-tert-butylphenyl)-2-methylpropyl]piperidine,
1-[2-(2,4-dichlorophenyl)-4-ethyl-1,3-dioxolan-2-yl-ethyl]-1H-1,2,4-triazole
1-[2-(2,4-dichlorophenyl)-4-n-propyl-1,3-dioxolan-2 -yl-ethyl]-1H-1,2,4-triazole
N-(n-propyl)-N-(2,4,6-trichlorophenoxyethyl)-N'-imidazolylurea,
1-(4-chlorophenoxy)-3,3-dimethyl-1-(1H-1,2,4-triazol-1-yl)-2-butanone,
α-(2-chlorophenyl)-α-(4-chlorophenyl)-5-pyrimidinemethanol,
5-butyl-2-dimethylamino-4-hydroxy-6-methylpyrimidine,
bis(p-chlorophenyl)-3-pyridinemethanol,
1,2-bis(3-ethoxycarbonyl-2-thioureido)benzene,
1,2-bis(3-methoxycarbonyl-2-thioureido)benzene, and also various fungicides, such as
dodecylguanidine acetate,
3-[3-(3,5-dimethyl-2-oxycyclohexyl)-2-hydroxyethyl] glutarimide, hexachlorobenzene,
DL-methyl-N-(2,6-dimethylphenyl)-N-2-furoyl alaninate,
DL-N-(2,6-dimethylphenyl)-N-(2'-methoxyacetyl)alanine methyl ester,
N-(2,6-dimethylphenyl)-N-chloroacetyl-D,L-2-aminobutyrolactone,
DL-N-(2,6-dimethylphenyl)-N-(phenylacetyl)alanine methyl ester,
5-methyl-5-vinyl-3-(3,5-dichlorophenyl)-2,4-dioxo-1,3-oxazolidine- 3-(3,5-dichlorophenyl)-5-methyl-5-methoxymethyl-1,3-oxazolidine-2,4-dione,
3-(3,5-dichlorophenyl)-1-isopropylcarbamoylhydantoin,
N-(3,5-dichlorophenyl)-1,2-dimethylcyclopropane-1,2-dicarboximide,
2-cyano[N-(ethylaminocarbonyl)-2-methoximino]acetamide,
1-[2-(2,4-dichlorophenyl)pentyl]-1H-1,2,4-triazole,
2,4-difluoro-α-(1H-1,2,4-triazolyl-1-methyl)benzhydryl alcohol,
N-(3-chloro-2,6-dinitro-4-trifluoromethylphenyl)-5-trifluoromethyl-3-chloro-2-aminopyridine,
1-(bis(4-fluorophenyl)methylsilyl)methyl)-1H-1,2,4-triazole.

Use Example 2-(2,4-Dimethylanilino)3-cyano-4,6-dimethylpyridine (A) and 2-(4-methoxyanilino)-3-cyano-4,6-dimethylpyridine (B), both disclosed in DE 3 731 626, were used as comparison active substances.

Use Example 1

Activity against *Botrytis cinerea* on bell peppers

Slices of green bell peppers were sprayed until dripping wet with aqueous active compound preparation which contained 80% active compound and 20% emulsifier in the dry matter. 2 hours after the spray coating had dried on, the fruit slices were inoculated with a spore suspension of *Botrytis cinerea* which contained $1.7 \times 10^6$ spores per ml of a 2% strength biomalt solution. The inoculated fruit slices were then incubated at 18° C. for 4 days in moist chambers. The assessment of the Botrytis development on the attacked fruit slices was then carried out visually.

The result shows that the active compound 532 when used as a 125 ppm active compound-containing spray liquor exhibits a better fungicidal action (5% attack of the fruit) than the known comparison active compounds A and B (90% attack of the fruit).

The result shows that the active compound 532 when used as a 125 ppm active compound-containing spray liquor exhibits a better fungicidal action (5% attack of the fruit) than the known comparison active compounds A and B (90% attack of the fruit).

We claim:
1. A 2-anilinopyridine of the formula I

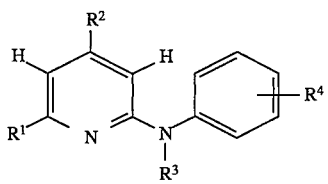

(I)

where the substituents have the following meanings:

$R^1$ is $C_1$–$C_6$-alkyl, $C_2$–$C_4$-alkenyl, $C_2$–$C_4$-alkynyl, $C_1$–$C_6$-haloalkyl, $C_1$–$C_6$-alkoxy-$C_1$–$C_6$-alkyl, $C_1$–$C_6$-alkylthio-$C_1$–$C_6$-alkyl or $C_3$–$C_6$-cycloalkyl; $C_3$–$C_6$-cycloalkyl, $C_1$–$C_6$-alkoxy or $C_1$–$C_6$-haloalkoxy substituted up to three times by identical or different $C_1$–$C_2$-alkyl or halogen substituents;

$C_1$–$C_2$-alkyl, $C_2$–$C_4$-alkenyloxy or $C_2$–$C_4$-alkynyloxy substituted by hydroxyl;

halogen, CN, SCN, formyl, CH=NOR$^5$, CH=NR$^6$ or CH$_2$NHR$^6$ $R^5$ is hydrogen or $C_1$–$C_8$-alkyl;

$C_1$–$C_4$-alkyl which is substituted by halogen, hydroxyl, cyano, $C_1$–$C_4$-alkoxy, COOC$_1$–$C_3$-alkyl or by phenyl, it being possible for the phenyl to be substituted by halogen, $C_1$–$C_3$-alkyl, $C_1$–$C_3$-alkoxy or nitro;

$C_3$–$C_6$-alkenyl, $C_3$–$C_6$-alkenyl substituted by halogen, $C_3$–$C_6$-alkynyl or $C_3$–$C_6$-alkynyl substituted by halogen, phenyl or phenyl substituted one to three times by halogen, $C_1$–$C_3$-alkyl, $C_1$–$C_3$-alkoxy or nitro or an acyl radical COR$^7$ where $R^7$ is $C_1$–$C_6$-alkyl or $C_1$–$C_6$-alkyl substituted by halogen or $C_1$–$C_3$-alkoxy, $C_3$–$C_6$-alkenyl or $C_3$–$C_6$-alkenyl substituted by halogen;

$R^6$ is hydrogen or $C_1$–$C_6$-alkyl, $C_1$–$C_4$-alkyl which is substituted by halogen, hydroxyl, cyano, $C_1$–$C_4$-alkoxy, $C_1$–$C_4$-alkylamino, $C_3$–$C_6$-cycloalkyl or by phenyl, it being possible for the phenyl to be substituted by halogen, $C_1$–$C_3$-alkyl, $C_1$–$C_3$-alkoxy or nitro;

$C_3$–$C_6$-cycloalkyl or $C_3$–$C_6$-cycloalkyl substituted by methyl, $C_3$–$C_6$-alkenyl or $C_3$–$C_6$-alkenyl substituted by halogen, $C_3$–$C_6$-alkynyl or $C_3$–$C_6$-alkynyl substituted by halogen;

phenyl or phenyl substituted by halogen, $C_1$–$C_3$-alkyl, $C_1$–$C_3$-alkoxy, $C_1$–$C_2$-haloalkyl, $C_1$–$C_2$-haloalkoxy or nitro;

$R^2$ is $C_1$–$C_6$-alkyl, $C_2$–$C_4$-alkenyl, $C_2$–$C_4$-alkynyl, $C_1$–$C_6$-haloalkyl, $C_3$–$C_6$-cycloalkyl or $C_3$$C_6$-cycloalkyl substituted up to three times by identical or different $C_1$–$C_2$-alkyl or halogen substituents, $R^8$ is hydrogen, CN, S(O)$_n$R$^8$ where n=0, 1 or 2, or COR$^9$ $R^8$ is $C_1$–$C_3$-alkyl, or phenyl, optionally substituted 1 to 3 times by halogen, $C_1$–$C_2$-alkyl, $C_1$–$C_2$-haloalkyl, methoxy or nitro, $R^9$ is hydrogen, $C_1$–$C_6$-alkyl, $C_1$–$C_6$-haloalkyl, $C_3$–$C_6$-cycloalkyl, phenyl or benzyl, or phenyl substituted 1 to 3 times by halogen, $C_1$–$C_3$ alkyl, $C_1$–$C_3$-haloalkyl, $C_1$–$C_3$-alkoxy, nitro or cyano, or benzyl substituted by these radicals, $R^4$ is hydrogen, halogen, $C_1$–$C_3$-alkyl, $C_1$–$C_2$-haloalkyl, $C_1$–$C_3$-alkoxy or $C_1$–$C_3$-haloalkoxy or cyano with the proviso that:

a) $R^1$ is not $C_1$–$C_4$-alkyl, $C_1$–$C_4$-alkoxy, $C_1$–$C_4$-haloalkyl, $C_1$–$C_4$-haloalkoxy, $C_3$–$C_6$-cycloalkyl, halogen or cyano, when $R^2$ is $C_1$–$C_4$-alkyl, $C_1$–$C_4$-haloalkyl or $C_3$–$C_6$-cycloalkyl and $R^3$ is hydrogen, b) $R^1$ is not methyl, when $R^2$ is methyl, $R^3$ is cyano and $R^4$ is hydrogen, and c) $R^1$ is not methyl, when $R^2$ is methyl, $R^3$ is phenyl—CO— and $R^4$ is hydrogen.

2. A compound of the formula I as in claim 1, where $R^1$ is cyclopropyl, $R^2$ is methyl, $R^4$ is hydrogen and $R^3$ is tosylsulfonyl (4—CH$_3$—C$_6$H$_4$—SO$_2$).

3. The compound, 2-anilino-6-cyclopropyl-4-methylpyridine.

\* \* \* \* \*

UNITED STATES PATENT AND TRADEMARK OFFICE
CERTIFICATE OF CORRECTION

PATENT NO.: 5,569,765

DATED: October 29, 1996

INVENTOR(S): WAGNER et al.

It is certified that error appears in the above-identified patent and that said Letters Patent is hereby corrected as shown below:

Column 36, claim 1, line 12, "$R^8$", first occurrence, should read --$R^3$--.

Signed and Sealed this

Twenty-fourth Day of December, 1996

Attest:

BRUCE LEHMAN

*Attesting Officer*     *Commissioner of Patents and Trademarks*